(12) United States Patent
Soman et al.

(10) Patent No.: US 11,926,847 B2
(45) Date of Patent: Mar. 12, 2024

(54) SELECTIVE ENRICHMENT OF HIGH-QUALITY DNA INTACT SPERMS FROM A SEMEN SAMPLE

(71) Applicant: Sanzyme Biologics Private Limited, Hyderabad (IN)

(72) Inventors: Raunak Jay Soman, Hyderabad (IN); Jay Soman, Hyderabad (IN); Motukuri Mahesh, Hyderabad (IN)

(73) Assignee: Sanzyme Biologics Private Limited, Hyderabad (IN)

( * ) Notice: Subject to any disclaimer, the term of this patent is extended or adjusted under 35 U.S.C. 154(b) by 643 days.

(21) Appl. No.: 17/045,471

(22) PCT Filed: Apr. 3, 2019

(86) PCT No.: PCT/IN2019/050274
§ 371 (c)(1),
(2) Date: Oct. 5, 2020

(87) PCT Pub. No.: WO2019/193603
PCT Pub. Date: Oct. 10, 2019

(65) Prior Publication Data
US 2021/0155898 A1  May 27, 2021

(30) Foreign Application Priority Data
Apr. 5, 2018 (IN) .............................. 201841004521

(51) Int. Cl.
*C12N 5/076* (2010.01)
*C12N 5/071* (2010.01)

(52) U.S. Cl.
CPC ........... *C12N 5/061* (2013.01); *C12N 5/0612* (2013.01); *C12N 2500/05* (2013.01); *C12N 2500/14* (2013.01); *C12N 2500/16* (2013.01); *C12N 2500/30* (2013.01); *C12N 2500/32* (2013.01); *C12N 2500/50* (2013.01); *C12N 2500/84* (2013.01)

(58) Field of Classification Search
CPC .. C12N 5/061; C12N 5/0612; C12N 2500/05; C12N 2500/14; C12N 2500/16; C12N 2500/30; C12N 2500/32; C12N 2500/50; C12N 2500/84
See application file for complete search history.

(56) References Cited

U.S. PATENT DOCUMENTS

2008/0200548 A1* 8/2008 Goldstein .............. C12N 5/061
600/35
2019/0136182 A1* 5/2019 Truong ................ C12N 5/0608

OTHER PUBLICATIONS

Lindholmer C. et al., Eliasson R. The effects of albumin magnesium and zinc on human sperm survival in different fractions of split ejaculates. Fertility and sterility. May 1, 1974; 25(5):424-31.
Urry R.et al. "The effect of single-density bovine serum albumin columns on sperm concentration, motility, and morphology" Fertility and sterility Nov. 1, 1983;40(5):666-9.
Malvezzi, H. et al., "Sperm quality after density gradient centrifugation with three commercially available media: a controlled trial" Reproductive Biology and Endocrinology. Dec. 2014;12(1):121.
Cheng M. et al. "The value of a commercial PVP solution as a modifier of sperm motility in the clinical ICSI procedure" Fertility and Sterility. Sep. 1, 2007;88:S360-1.
Lopez, G. et al. "Diagnostic value of sperm DNA fragmentation and sperm high-magnification for predicting outcome of assisted reproduction treatment" Asian Journal of Andrology; 2013 (15); 790-794.
He, M. et al. "Correlation between sperm ultrastructure in infertile patients with abnormal sperm morphology and DNA damage" Genet. Mol. Res. 14 (4); (2015) 17000-17006.

* cited by examiner

*Primary Examiner* — Kara D Johnson
(74) *Attorney, Agent, or Firm* — Amin Talati Wasserman LLP; George M. Carrera, Jr.; Valerie Neymeyer-Tynkov (57) ABSTRACT

Disclosed is a composition for selective enrichment of progressively motile non-fragmented/intact DNA sperms during swim-up of semen sample comprising combination of electrolytes, a mix of excipients, polyvinylpyrrolidone, recombinant human serum albumin or bovine serum albumin. A method of selective enrichment of DNA-intact sperms using the compositions of the present invention is also disclosed. The DNA fragmentation index of the swim-up sperms are less than the DNA fragmentation index of the neat samples. The media compositions of the present invention are applicable for enrichment of non-fragmented/intact DNA sperms for therapeutic purposes in the field of assisted reproductive technologies.

4 Claims, 9 Drawing Sheets

SELECTIVE ENRICHMENT OF HIGH-QUALITY DNA INTACT SPERMS FROM A SEMEN SAMPLE

FIELD OF THE INVENTION

The invention relates to enhanced separation and/or enrichment of fractions containing relatively higher proportion of sperms with normal morphology and intact or non-fragmented DNA from the semen for the therapeutic use like in-vitro fertilisation (IVF) or intra cytoplasmic sperm injection (ICSI) or Intracytoplasmic morphologically selected sperm injection (IMSI) and other treatment options of assisted reproductive technologies (ART) including Gamete intra fallopian transfer (GIFT), Zygote intra fallopian transfer (ZIFT).

BACKGROUND OF THE INVENTION

In general, the semen quality is determined by the concentration, motility and morphology of the spermatozoa and the consistency and volume of the semen. As a part of infertility treatment Assisted Reproductive Technologies like IUI, IVF & ICSI use the motile spermatozoa separated from the rest of the components of semen in order to fertilize for the in-vitro fertilization of oocytes.

Sperms can be separated from the semen by various separation techniques that depend on sperm motility parameter. The total separation or yield is directly proportional to the number of motile sperms in Neat Sample.

In IUI or IVF—even though high yield of sperm matters most to execute the procedure; the final outcome depends on the DNA integrity of the sperm that fertilise the oocyte. Yield of Sperms refers to the number of sperms that comes up at the end of the swim-up procedure. Swim-up refers to the process of sperm separation from the Semen where semen sample is kept in the bottom of a test tube and the media will be layered on top of the semen sample. Swim-up happens naturally and it depends on the capability of sperm (motility) and physico-chemical properties of media. Good sperms exhibit progressive mobility, good morphology with respect to their head, neck and tail, having acrosome cap, presence of vacuole, and non-fragmented/intact DNA.

A minimum of 1.5 million sperms are need for insemination (IUI) after the separation for giving a successful pregnancy. In IVF, 30-40 thousand sperms are required for each oocyte to inseminate in the petri dish. For example, 0.3-0.4 millions of sperms are needed to inseminate 10 oocytes. In ICSI it is desirable to have high percentage of good (non-fragmented) DNA sperms to enhance the success rate of the treatment.

DFI (DNA Fragmentation Index) is one of the important factors that determines the developmental competency of fertilized oocytes and subsequent implantation or pregnancy rates after the ART treatment [Gemma Lopez, Rafael Lafuente, Miguel A Checa, Ramon Carreras, and Mario Brassesco; Asian J Androl.; 15(6): 790-794 (2013)]. Correlation between sperm ultrastructure in infertile patients with abnormal sperm morphology and DNA damage has been established [M. He and L. Tan; Genetics and Molecular Research 14 (4): 17000-17006 (2015)]

Standard methods for sperm preparation techniques such as density gradient centrifugation (DGC) and swim-up (SU) techniques are in common practice of sperm preparation for ART. DNA damage may occur during sperm processing either due to increased ROS levels or prolonged exposure to the media and uncontrolled environment. DNA damage negatively influences the sperm fertilization ability.

If the number of intact DNA sperms are separated and inseminated from the sample of high DFI, there could be a significant change in embryo quality and the formation of balstocyst and subsequent implantation or pregnancy rates.

The commonly used media for the preparation of sperms are developed from base formulations such as HBSS (Hank's Balanced Salt Solution), EBSS (Earl's Balanced Salt Solution), DMEM (Dulbecco's Modified Eagles Media), HTF (Human Tubal Fluid) and m-HTF (modified-HTF). Commercially available formulations using the above said base media compositions with added ingredients like gentamicin, human serum albumin, sodium hyaluronan or anti-oxidants like sodium pyruvate or receptor binding agents like Glutamine or chelators such as EDTA for improving the fertilization rates and reducing the ROS thereby delaying the process of DNA fragmentation.

The challenge has been in tailoring media and methods to enhance separation and/or enrichment of fractions containing relatively high proportions of non-DNA fragmented sperms and collection of such sperms in adequate numbers for doing IUI, IVF or ICSI. There is therefore an unmet need to provide media that would ensure separation and/or enrichment of fractions containing relatively high proportions of non-DNA fragmented sperms with normal morphology and high proportions of non-DNA fragmented sperms.

The present invention precisely provides the media that is judiciously formulated to ensure enhanced separation and/or enrichment of fractions containing relatively high proportions of non-DNA fragmented sperms with normal morphology and normal DNA when semen is subjected to a direct swim-up treatment. The present invention also addresses issues related to OAT (oligoasthenoteratozoospermia) patients.

OBJECTS OF THE INVENTION

The main object of the invention is to provide a swim-up medium to enable and facilitate the enrichment of fractions with sperms that are normal with genetically intact DNA when subjected to swim-up in the said medium.

Another object of the invention is to provide a judiciously prepared medium to enable the yield of maximal number of genetically competent sperms from a semen sample.

SUMMARY OF THE INVENTION

In accordance with the invention, a swim-up medium for enrichment of fractions containing DNA-intact sperms post swim-up, from a semen sample, the swim-up medium prepared from a solute composition comprising:
(a) electrolytes, wherein the said electrolytes are present from 10% w/w to 50% w/w, the electrolytes selected from a group of halides such as sodium chloride, potassium chloride, calcium chloride, magnesium chloride; metal sulphates such as magnesium sulphate; phosphates such as potassium di-hydrogen orthophosphate, sodium phosphate mono basic; sodium bicarbonate, glucose, and combinations thereof;
(b) excipients from 1% to 30% w/w selected from phenol red, HEPES buffer, gentamicin, sodium pyruvate, sodium lactate, glutamine, glycine, L-arginine, and methionine and combinations thereof;
(c) Polyvinylpyrroliidone (PVP) or from 1% w/w to 80% w/w);
(d) recombinant Human Serum Albumin (rHSA) or bovine serum albumin (BSA) from 0.1% w/w to 50% w/w;
wherein the said solute is dissolved in water to resulting in a 0.5-15% w/v solution.

Another aspect of the invention, a method of enrichment of fractions containing DNA-intact sperms from a sperm sample is provided when a sperm sample is subjected to swim-up in the medium of the present invention, wherein the DFI of the sperms after swim-up in the said medium is less than the DFI of the sperms in the neat samples.

In another aspect of the invention, method of preparation of the said medium and a process of swim-up of sperms using the said medium is disclosed.

In yet another aspect of the invention, comparative results of post swim-up DFI of semen samples in the medium of the present invention with the post swim-up of the same samples in a commercial medium is provided.

DETAILED DESCRIPTION OF THE INVENTION

It has surprisingly been found that swim-up media compositions comprising combination with Poly Vinyl Pyrrolidone (PVP), and Human Serum Albumin (HSA) or Bovine Serum Albumin (BSA), electrolytes and excipients, can enrich post swim-up fractions with highly progressive spermatozoa in a swim-up process in the said medium.

It was further been surprisingly found that, the media prepared from the solute compositions of the present invention provide higher yield of non-fragmented/intact DNA sperms in post swim-up fractions.

In accordance with the invention, a swim-up medium for enrichment of post swim-up fractions containing DNA-intact sperms from a semen sample, the swim-up medium is prepared from a solute composition comprising:
(a) electrolytes, wherein the said electrolytes are present from 10% w/w to 50% w/w, the electrolytes selected from a group of halides such as sodium chloride, potassium chloride, calcium chloride, magnesium chloride; metal sulphates such as magnesium sulphate; phosphates such as potassium di-hydrogen orthophosphate, sodium phosphate mono basic; sodium bicarbonate, glucose, and combinations thereof;
(b) excipients from 1% to 30% w/w selected from phenol red, HEPES buffer, gentamicin, sodium pyruvate, sodium lactate, glutamine, glycine, L-arginine, and methionine and combinations thereof;
(c) Polyvinylpyrroliidone (PVP) or from 1% w/w to 80% w/w);
(d) recombinant Human Serum Albumin (rHSA) or bovine serum albumin (BSA) from 0.1% w/w to 50% w/w;
wherein the said solute is dissolved in water resulting in solution with upto 15% w/v of the solute.

The medium is sterilised by filtration through 0.2 micron filter and stored at 2-8° C. to minimise bacterial growth.

Sperms are subjected to swim-up and the fraction of the sperms post swim-up are tested for sperm DNA fragmentation using the Halo Sperm method with Sperm Chroma Kit [Journal of Andrology, Vol. 27, No. 1, January/February 2006; 10.2164/jandrol.05068]. In this method the sperm with big halos are non-fragmented/intact DNA and sperms with medium-small and no halo represent DNA fragmentation to varying extent.

The invention is illustrated with non-limiting examples.

Example 1: Preparation of SNZ-Plain Medium

A typical SNZ-PLAIN solute comprises electrolytes (approximately 70% w/w %) and mix of excipients phenol red, HEPES buffer, Gentamicin, Sodium Pyruvate, Sodium lactate, glutamine, Glycine, L-Arginine, and methionine (approximately 30 w/w %). This solute when dissolved in water results ~1.7% w/v % solution, which is used as swim-up medium for the experiments.

The electrolytes comprises Sodium chloride (75.6 w/w %), potassium chloride (3.4 w/w %), magnesium sulfate dried (0.4 w/w %), potassium dihydrogen ortho-phosphate (0.5 w/w %), calcium chloride (0.3 w/w %), sodium bicarbonate (2.9 w/w %), sodium phosphate mono basic, anhydrous (0.3 w/w %), glucose (15.5 w/w %), magnesium chloride (0.9 w/w %). This solute when dissolved in water results in ~1.2 w/v % solution The medium is sterilized by filtration through 0.2 micron filter and stored at 2-8° C. to minimize and avoid bacterial growth or contamination.

Example 2: Preparation of "SNZ-Plus" Media of the Present Invention 2.1 Preparation of "SNZ-Plus" Sperm Swim-Up Media with Bovine Serum Albumin A typical SNZ plus solute comprises electrolytes (approximately 44% w/w), excipients mix of phenol red HEPES buffer, gentamicin, sodium pyruvate, sodium lactate, glutamine, glycine, L-arginine, and methionine (approximately between 9% w/w), PVP (~30 w/w %), BSA (approximately 16 w/w %). This solute when dissolved in water results in ~3 w/v % solution used for the experiments, in which PVP is ~1 w/v % and BSA is ~0.5 w/v %.

The electrolytes comprise sodium chloride (75.6 w/w %), potassium chloride (3.4 w/w %), magnesium sulfate (0.4 w/w %), potassium dihydrogen orthophosphate (0.5 w/w %), calcium chloride (0.3 w/w %), sodium bicarbonate (2.9 w/w %), sodium phosphate mono basic, anhydrous (0.3 w/w %), glucose (15.5 w/w %), magnesium chloride (0.9 w/w %). This solute when dissolved in water results in ~1.2 w/v % solution.

The pH of the solution is adjusted to pH 7.2-7.6 (the medium). The medium is sterilised by filtration through 0.2 micron filter and stored at 2-8° C. to minimize or avoid bacterial growth or contamination of any nature.

Example 2.2. Preparation of SNZ-Plus Sperm Swim-Up Media with Recombinant Human Serum Albumin and Polyvinylpyrrolidone Typical SNZ plus solute compositions comprise electrolytes (5%-65% w/w), excipients comprising phenol red, HEPES buffer, gentamicin, sodium pyruvate, sodium lactate, glutamine, glycine, L-arginine, and methionine (1% to 30% w/w), PVP (1% to 80% w/w), recombinant HSA (0.1% to 50% w/w). These solute compositions when dissolved in water results in 0.1%-15% w/v medium solution used for the swim-up experiments, in which PVP ranges from 0.1% to 10% w/v and rHSA is between 0.05% to 2% w/v. The electrolyte composition is sodium chloride (75.6 w/w %), potassium chloride (3.4 w/w %), magnesium sulphate dried (0.4 w/w %), potassium di-hydrogen orthophosphate (0.5 w/w %), calcium chloride (0.29 w/w %), sodium bicarbonate (2.9 w/w %), sodium phosphate mono basic anhydrous (0.3 w/w %), glucose (15.5 w/w %), magnesium chloride (0.9 w/w %). A set of SNZ-Plus media with varying concentrations of the solute compositions were prepared and named as given in Table 1.

Thus, disclosed is a process for the preparation of the swim-up medium (SNZ-Plus) of the present invention for selective enrichment of fractions containing DNA-intact sperms post swim-up, from semen, in steps comprising:
  Dissolving the solute composition in water for injection to obtain a swim-up medium of 1 to 15% w/v solution,
  Adjusting the pH of the solution to pH 7.2 to 7.6,
  Filtering through 0.2 micron filter and bottled in aseptic conditions, Storing the solution at 2-8° C.

These SNZ-Plus media were used for the comparative swim-up experiments mentioned in the subsequent examples.

TABLE 1

Compositions of SNZ Plus Solutes and SNZ Plus media

| Name of | Composition of the Solute (w/w) | | | |
|---|---|---|---|---|
| No. | SNZ Plus Medium | Electrolytes (w/w %) | Excipients (w/w %) | rHSA (w/w %) | PVP (w/w %) |
| 1 | VH39 | 35.86 | 16.12 | 1.54 | 46.45 |
| 2 | JI24 | 24.49 | 11.01 | 1.05 | 63.44 |
| 3 | LO12 | 17.21 | 7.73 | 0.74 | 74.3 |
| 4 | SW20 | 45.79 | 20.59 | 29.65 | 3.95 |
| 5 | UI19 | 29.47 | 13.25 | 19.08 | 38.17 |
| 6 | WY89 | 21.33 | 9.59 | 13.81 | 55.26 |
| 7 | SO56 | 15.58 | 7 | 10.09 | 67.3 |
| 8 | IX90 | 31.48 | 14.15 | 40.77 | 13.59 |
| 9 | RD21 | 14.15 | 6.36 | 18.34 | 61.13 |
| 10 | TR77 | 24.75 | 11.12 | 32.05 | 32.05 |

Example 3: Selection of Neat Semen Samples

The semen samples selected in the context of the present invention are those that meet the following criteria:

TABLE 2

Semen selection parameters

| | Parameters | Minimum requirements |
|---|---|---|
| 1 | Volume | 1 ml or above |
| 2 | Count | 15 million/ml or above |
| 3 | Motility (total) | 20% or above |
| 4 | Progressive motility | 10% or above |
| 5 | Morphology | 4% good and above |
| 6 | Aggregation of sperms | Present |
| 7 | Round cells/epithelial cells/debris | Present |
| 8 | Viscosity | Mild to moderate |
| 9 | DFI Neat | Preferably 50 or above |
| 10 | Virus Tests (HIV, HbsAg, HCV, VDRL) | Negative |

Semen samples were collected from Volunteer A, Volunteer B, and Volunteer C at different times. The semen ejaculated from these said Volunteers A, B and C were subjected to the criteria in Table 2 and the samples that met all the criteria were selected for the swim-up experiments in various media.

Example 4: Comparative SWIM-UP Results of Semen Samples in SNZ-Plus Media, in SNZ-Plain and in Commercial Media After liquefaction of the semen samples obtained in the above example 1, the semen was mixed to make it homogenous. A standard semen analysis performed using Makler Chamber. Direct Swim-up method (without centrifugation) is used for the separation. Semen sample will be under-layed in a test tube containing medium (prepared from the solute compositions as disclosed in Table 1 above) for swim-up. A standard diameter of 1.1 cm as inner diameter is used in all experiments. Temperature was maintained at 37° C. The tubes were incubated at an inclination of 45 degrees without disturbing the layers of semen and medium. The inclination offers maximum cross-sectional area to the semen and medium so that a greater number of sperms can have access to the medium for the swim-up.

Swim-ups were conducted with a single sample divided into equal parts after the analysis of the neat semen sample meeting the criteria as provided in Table 2. Swim-up was conducted in different media viz., "SNZ Plus" media (with Bovine serum albumin and Polyvinylpyrollidone prepared according to Example 2.1), "SNZ-Plus" media (with various range of solute compositions prepared according to Example 2.2); "SNZ Plain" medium (of Example 1) and/or a commercially available medium.

0.3 ml of Semen sample was used for the swim-up experiments with 0.7 ml of commercially available medium, SNZ plain medium and SNZ plus media (with either BSA or rHSA and PVP) with the incubation time of 30 minutes at 37° C. After 30 minutes, 0.2 ml was recovered from the top portion for analysing swim-up following the swim-up the sperms are subjected to DNA halo test.

As per the method of the present invention, swim-up was also performed in several SNZ Plus media wherein BSA was replaced by rHSA and the media contained both rHSA and PVP.

Thus, as per the methods of the present invention, a process of swim-up of sperms using the medium of the present invention is disclosed, comprising the steps of:
(i) taking a standard sterile test tube of 11 mm diameter used for all swim-ups;
(ii) Collecting neat semen sample from a Volunteer and liquifying the same for 30-45 minutes;
(iii) Dispensing 0.7 ml of pre-heated SNZ Plus media of the present invention into a test tube of 11 mm diameter;
(iv) Loading 0.3 ml of thoroughly mixed liquified neat sample of step (ii) above at the bottom of the test tube;
(v) Inclining the test tube to about 45 degrees at 37° C. and in a highly humid environment for 30 mins for selective enrichment of the DNA intact sperms through swim-up of the sperms;
(vi) Collecting 200 micro litres of swim-up fraction containing DNA-intact sperms from the top layer of the test tube and keeping it at room temperature in 0.5 ml eppendorf tube for DNA fragmentation test:
(vii) Storing the selectively enriched fractions containing DNA-intact sperms post swim-up wherein the $DFI_{post\ swimup} < DFI_{neat}$ for further use.

After swim-up, the sperms were assessed for DNA Fragmentation using Sperm Chromatin Dispersion test (SCD) and DFI is estimated using conventional bright-field microscopy. The commercially available kit has pre-coated slide, solution A (denaturing solution), solution B (lysis solution), solution C (Phosphate Buffer Saline or a diluent) and solution D (staining solution).

As per the recommended procedure (SCD), the semen sample (after swim-up collected from the top of the test tube) is diluted with culture medium to 5-10 M/ml. The agarose is melted at 90° C. in the Sperm Chroma warmer-1 for 5 minutes and transferred the agarose to the sperm chroma warmer-2 that was maintained at 37° C. and waited for 5 minutes. Added 25 micro-liters of the sperm sample to agarose and mixed well. Placed the sperm cell suspension immediately onto the pre-treated slides and placed the cover-slip avoiding formation of air bubbles and left the slide at 4° C. for 5 minutes. Then the cover glass was removed by sliding it off gently taking care to maintain the slide in a horizontal position throughout the procedure. The slides were incubated horizontally in Solution A (denaturing solution) for 7 minutes followed by incubation in Solution B (lysis solution) for 25 minutes. The slides were left in distilled water for 5 minutes and then placed in 70% ethanol for 2 minutes, followed by 90% ethanol for 2 minutes and finally in 100% ethanol for 2 minutes. Then they were dried at room temperature. Mixed the solution C (Phosphate Buffer Saline or a Diluent) and Solution D (staining solution) at 1:1 ratio, and deposited a layer of stain, horizontally and left to stain for 15-20 minutes. Decanted the stain and gently washed with distilled water & dried at room temperature. Observed the slide under bright field microscope using 40× objective and graded the spermatozoa. Sperm DNA fragmentation index (DFI) calculation: Classified at least 300-500 sperms cells as follows

TABLE 3

Type and Characteristics of Halos

| | |
|---|---|
| Sperm without DNA fragmentation | a. Big Halo |
| | b. Medium Halo |
| Sperm with DNA fragmentation | c. Small Halo |
| | d. Without Halo |
| | e. Without Halo and degraded |

DFI (%) = 100 × No of sperm with fragmented DNA/Total number of sperms counted.

Example 4.1: Sperm SWIM-UP in SNZ-Plus Media Comprising BSA and PVP

Figure 1:
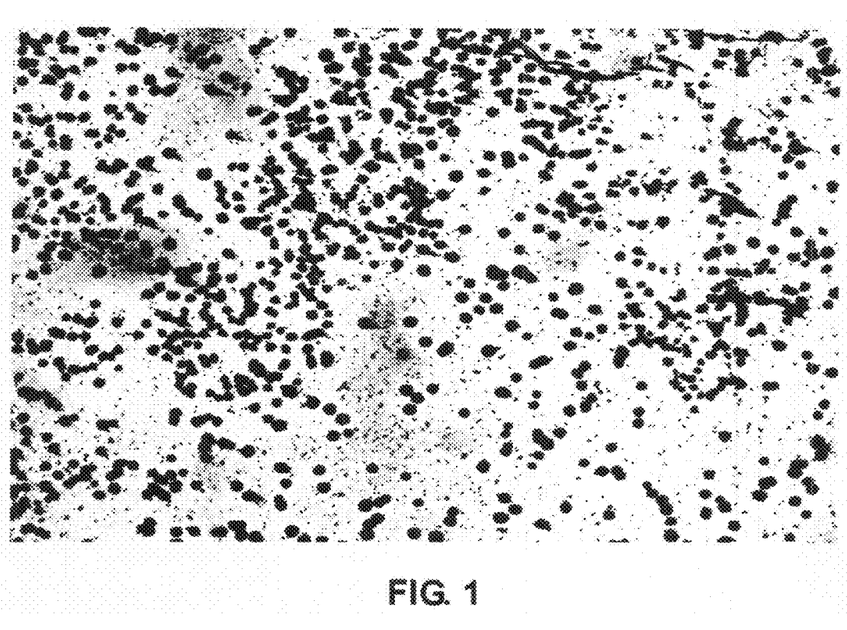
FIG. 1: Sperms with comparatively less number of non-fragmented/intact DNA in commercial medium after the swim-up. The presence of halos and the size denotes extent of DNA Fragmentation in the sperms (refer FIG. 3).
Figure 2:
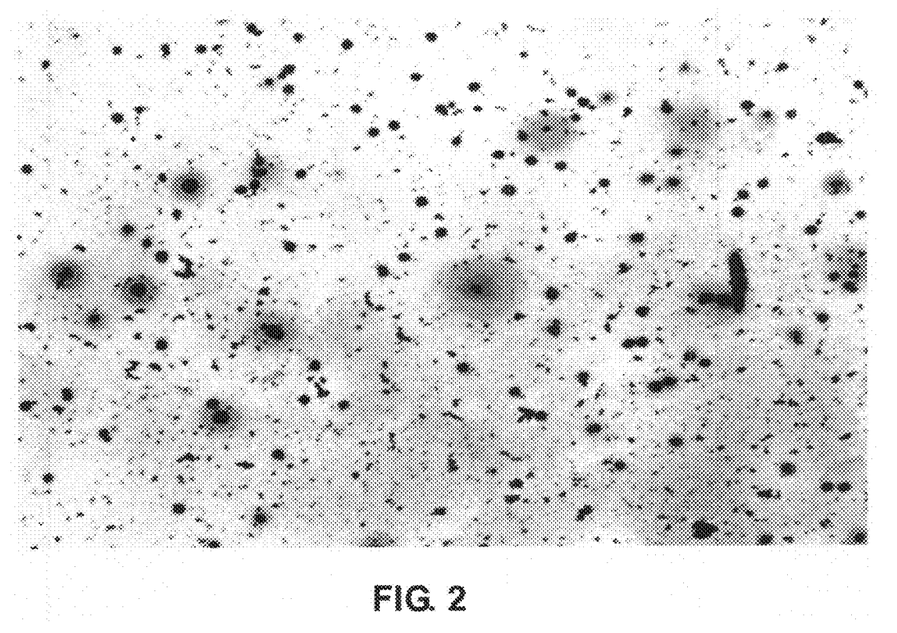
FIG. 2: Separated Sperms with higher number of non-fragmented/intact DNA in "SNZ-plus" medium after swim-up. The presence of halos and the size denotes extent of DNA Fragmentation in the sperms (refer FIG. 3).
Figure 3:
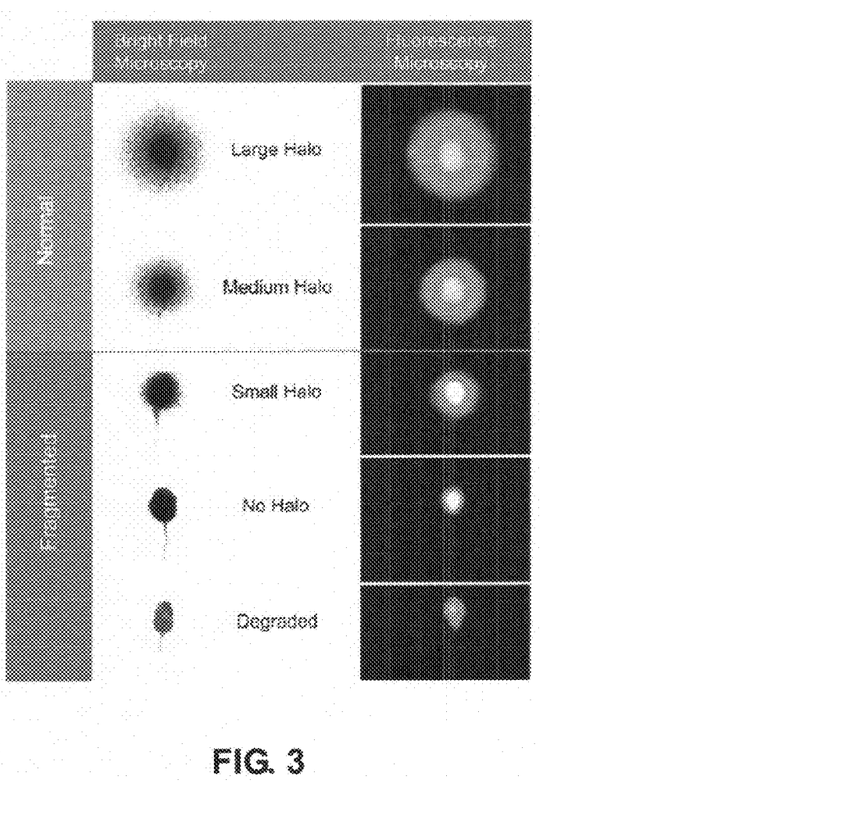
FIG. 3: Characterization of spermatozoa by SPERM CHROMATIN DISPERSION TEST (SCD) or HALO TEST.
Figure 4:
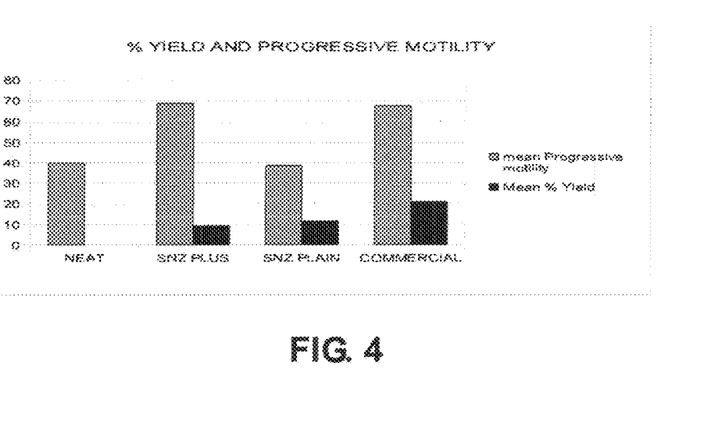
FIG. 4: Mean progressive motility and mean percentage yield of sperms in swim-up in SNZ-Plus (with Bovine Serum Albumin and Polyvinylpyrrolidone), SNZ Plain and Commercial medium (HEPES-HTF). The comparative yield of sperms post swim-up in SNZ Plus medium is less that in Commercial or SNZ Plain media. However, the mean progressive motility in the SNZ medium is marginally higher than the corresponding motility in Commercial medium.
Figure 5:
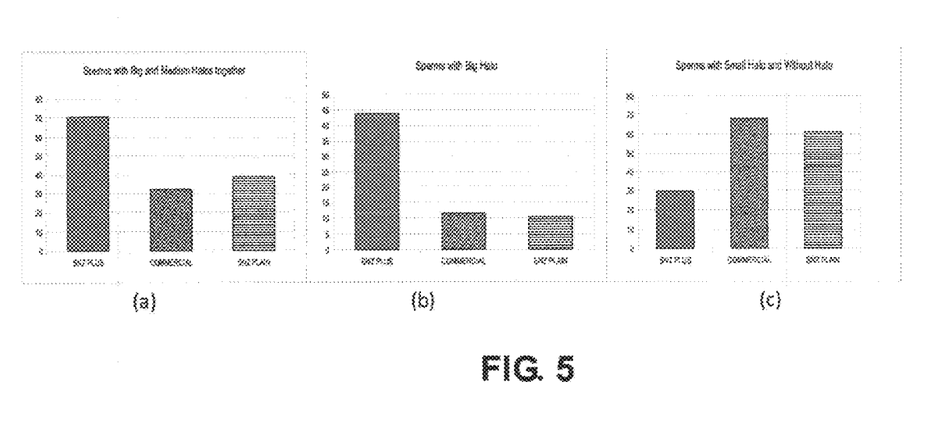
FIG. 5: Sperms post swim-up in SNZ-Plus (with Bovine serum albumin and Polyvinylpyrollidone), SNZ-plain and commercial medium showing big and medium type of halos (A+B), only Big-type Halos (A), small halo and no-halo (C+D). The number of big and medium type of halos or only big halos are considerably higher post swim-up in SNZ-Plus in comparison to those in SNZ-plain and/or the commercial medium.

Characterisation of Fractions of the Sperms Post Swim-Up in SNZ Plain, SNZ Plus with PVP and BSA and Commercial Media:

The commercial medium resulted more swim-up sperms than SNZ medium (FIG. 4). However, SNZ Plus medium with PVP & BSA scores 1.82 and 2.21 folds better when compared with SNZ-Plain and commercial media respectively (FIG. 5-a) for both big and medium halo spermatozoa. Further, the SNZ Plus Medium with PVP & BSA scores 4.2 and 3.86 folds better when compared with SNZ Medium and Commercial media respectively with respect to the Big halo spermatozoa (FIG. 5-b). The overall superior performance of the SNZ Plus medium with PVP and BSA is illustrated in the bar chart (FIG. 6) which clearly demonstrates the significantly lower DNA fragmentation as compared to the commercial and SNZ medium.

Similar experiments are conducted with two media viz., SNZ Plus and SNZ plain to assess effect of addition of PVP & BSA in the SNZ-Plus medium.

Figure 6:
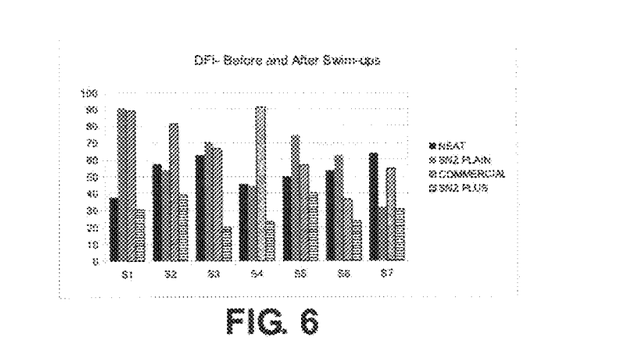
FIG. 6: Bar chart showing DFI of sperms in neat semen samples before swim-up and post swim-up in SNZ-Plus (with Bovine Serum Albumin and Polyvinylpyrollidone), SNZ-Plain and Commercial medium. DFI of the post swim-up fraction in the commercial medium increases when compared to the DFI of neat sample showing higher DNA fragmentation post swim-up, which is undesirable. The DFI of the post swim-up fraction in SNZ-Plus medium (with BSA and PVP) decreases with respect to the DFI of the neat semen sample. This shows that post swim-up fraction in the SNZ-Plus medium is enriched with relatively higher proportion of non-fragmented/intact DNA-sperms as compared to those in the neat semen sample.
Figure 7A:
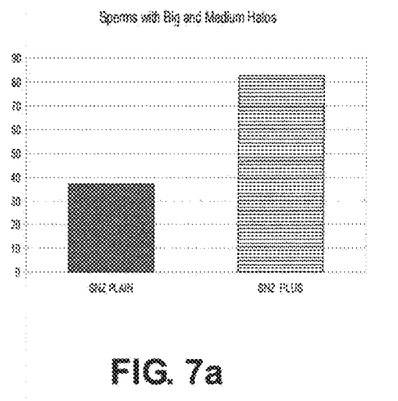
FIG. 7: Post swim up fractions in SNZ-Plus (with Bovine Serum Albumin and Polyvinylpyrrolidone) and SNZ-Plain medium showing big+medium type of halos (A+B) and only big halos (A).
Figure 7B:
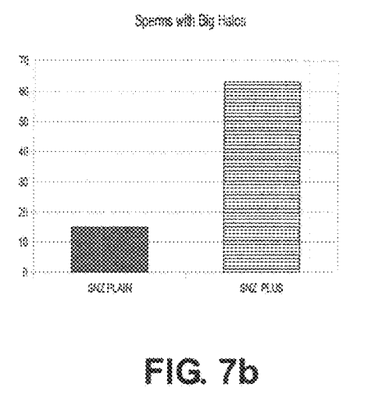
Figure 8:
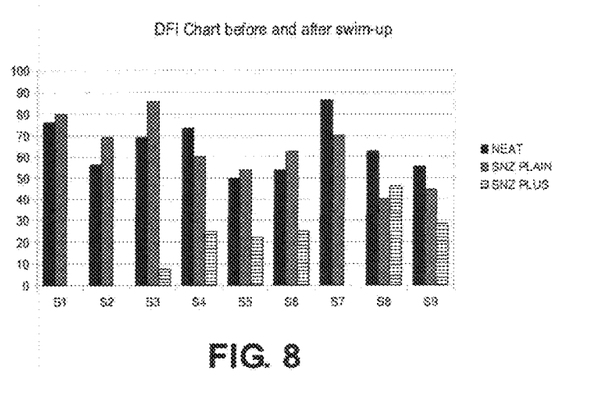
FIG. 8: Bar chart showing sperm DFI of semen samples (S1 to S9) before swim-up (the neat sample) and after swim-up in SNZ-Plus (with Bovine Serum Albumin and Polyvinylpyrrolidone), and in SNZ-Plain medium. The DFI of the samples increase after swim-up in the commercial medium in comparison with the DFI of the neat semen sample, which is undesirable. DFI of the samples decrease after swim-up in SNZ-Plus media (with BSA and PVP) illustrating the effect of BSA and PVP in the swim-up medium.
Figure 9:
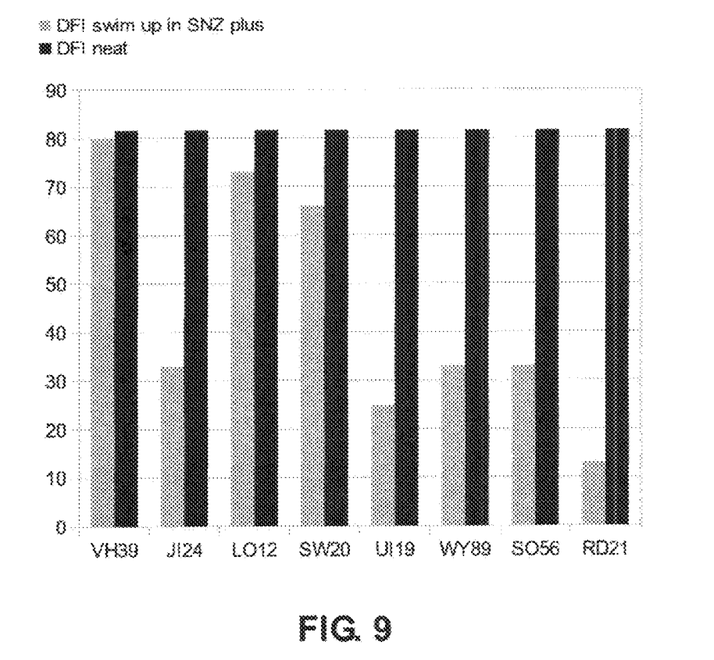
FIG. 9: Bar chart of DFI before and after swim-up in SNZ Plus media (VH39, J124, LO12, SW20, UI19, SO56, and RD21) in comparison with neat samples obtained from Volunteer A. It is observed that, $DFI_{SWIM-UP} < DFI_{NEAT}$ in SNZ Plus media.
Figure 10:
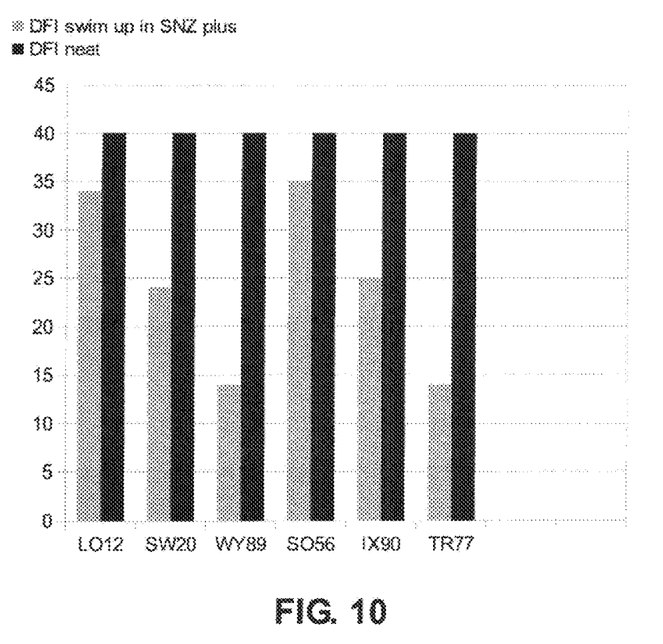
FIG. 10: Bar chart of DFI before and after swim-up in SNZ Plus media (LO12, SW20, WY89, SO56, IX90, TR77) in comparison with the DFI in SNZ Plain swim-up fraction and neat samples obtained from Volunteer B. $DFI_{SWIM-UP}$ in SNZ Plus media$<DFI_{NEAT}$.

The DNA fragmentation index (DFI) of the halo tests are given in FIGS. 6 and 8. In FIGS. 6 and 8, $DFI_{swim-up} < DFI_{neat}$ in SNZ-Plus media, whereas $DFI_{swim-up} > DFI_{neat}$ in commercial medium. SNZ Plus medium with PVP & BSA scores 2.23 folds better when compared with SNZ (Plain) (FIG. 7-$a$) for both big and medium halo spermatozoa.

Further, the SNZ Plus Medium with PVP & BSA scores 4.2 folds better when compared with SNZ plain Medium with respect to the Big halo spermatozoa (FIG. 7-$b$). The overall superior performance of the SNZ Plus medium with PVP and BSA is illustrated in the bar chart (FIG. 8) which clearly demonstrates significantly lower DNA fragmentation index (DFI) of swim-up sperms in SNZ Plus media as compared to the neat samples, as well as the higher DNA fragmentation index (DFI) of swim-up sperms in either SNZ Plain or commercial media as compared to the neat samples.

Example 4.2: SPERM SWIM-UP of Semen Samples Collected from Volunteers A, B and C in SNZ-Plus Media Comprising Recombinant Human Serum Albumin (rHSA) and Polyvinylpyrrolidone (PVP)

Experiments Using Semen Samples of Volunteer A

Semen samples was collected from Volunteer A and subjected to the selection criteria in table 2 set out in Example 3. Each neat sample with equal aliquots of the sample was subjected to swim-up in different SNZ-Plus media which contained varying concentrations of rHSA and PVP as disclosed in Table 1 in Example 2.2.

Post swim-up fractions of the sperms were assessed for DFI using Sperm Chromatin Dispersion Test (SCD). DFI of the sperms in neat samples obtained from Volunteer-A and the swim-up fractions post swim-up in SNZ-Plus media are presented in Table no 4. It is surprisingly found that $DFI_{swim-up} < DFI_{neat}$ in the SNZ-plus media comprising rHSA and PVP. This demonstrates that progressively motile DNA-intact sperms are enriched in the top swim-up layer of the sperms and if used in assisted reproductive methodologies has the potential to increase the chances of successful fertilization.

TABLE 4

Swim-up results of samples obtained from Volunteer A in SNZ-plus media vs. Neat (without swim-up).

| Parameters | Neat (Before Swim-up) | SNZ PLUS Medium | | | | | | | |
|---|---|---|---|---|---|---|---|---|---|
| | | VH39 | JI24 | LO12 | SW20 | UI19 | WY89 | SO56 | RD21 |
| Count (millions/ml) | 40 | 10 | 8 | 20 | 25 | 6 | 12 | 20 | 8 |
| Total Motility (%) | 30 | 98 | 95 | 100 | 100 | 100 | 80 | 100 | 98 |
| Progressive Motility (%) | 10 | 98 | 95 | 100 | 100 | 100 | 70 | 100 | 98 |
| Non-Progressive Motility (%) | 0 | 0 | 0 | 0 | 0 | 0 | 10 | 0 | 0 |
| Immotile (%) | 10 | 0 | 0 | 0 | 0 | 0 | 0 | 0 | 0 |
| Dead (%) | 60 | 2 | 5 | 0 | 0 | 20 | 0 | 0 | 2 |
| % Yield | 100 | 25 | 20 | 50 | 15 | 30 | 50 | 50 | 20 |
| % (Big Halos) | 5.6 | 0 | 0 | 0 | 33 | 0 | 0 | 0 | 50 |
| % (Big and Medium Halos) | 18.4 | 20 | 66.6 | 26.6 | 33 | 75 | 66 | 66 | 87 |
| DNA Fragmentation Index (DFI) | 81.6 | 80 | 33 | 73 | 66 | 25 | 33 | 33 | 13 |

Experiments Using Semen Samples of Volunteer B

The set of experiments as described in the case of Volunteer A were repeated with the samples obtained from Volunteer B. The results are presented in Table no 5. It is surprisingly observed that the $DFI_{swim-up} < DFI_{neat}$ in the SNZ-plus media prepared according to the compositions of Example 2.2. These results again confirm that progressively motile DNA-intact sperms are enriched in the top swim-up layer of the sperms and if used in assisted reproductive methodologies has the potential to enhance the probability of successful fertilisation.

TABLE 5

Results of swim-up with sample obtained from Volunteer B in SNZ-plus media vs. Neat (without swim-up)

| Parameters | Neat (no swim-up) | SNZ-Plus Medium | | | | | |
|---|---|---|---|---|---|---|---|
| | | LO12 | SW20 | WY89 | SO56 | IX90 | TR77 |
| COUNT (millions/ml) | 90 | 20 | 22 | 20 | 20 | 20 | 20 |
| Total Motility (%) | 50 | 100 | 100 | 100 | 100 | 100 | 100 |
| Progressive Motility (%) | 20 | 100 | 100 | 100 | 100 | 100 | 100 |
| Non-Progressive Motility (%) | 30 | 0 | 0 | 0 | 0 | 0 | 0 |
| Immotile (%) | 20 | 0 | 0 | 0 | 0 | 0 | 0 |
| Dead (%) | 30 | 0 | 0 | 0 | 0 | 0 | 0 |
| Yield (%) | 100 | 22 | 24 | 22 | 22 | 22 | 22 |
| % (Big Halos) | 8 | 0 | 10 | 18 | 2 | 5 | 21 |
| % (Big and Medium Halos) | 60 | 66 | 76 | 86 | 65 | 75 | 85 |

TABLE 5-continued

Results of swim-up with sample obtained from
Volunteer B in SNZ-plus media vs. Neat (without swim-up)

| Parameters | Neat (no swim-up) | SNZ-Plus Medium | | | | | |
|---|---|---|---|---|---|---|---|
| | | LO12 | SW20 | WY89 | SO56 | IX90 | TR77 |
| DNA Fragmentation Index (DFI) | 40 | 34 | 24 | 14 | 35 | 25 | 14 |

Experiments Using Semen Samples of Volunteer C

The set of experiments as described in the case of Volunteers A and B were repeated with the samples obtained from Volunteer C. The results are presented in Table no 6 and 7. In the case of samples from Volunteer C, additional swim-up experiments were also performed in SNZ-Plain medium and in a commercial medium.

It has surprisingly been found that, the $DFI_{swim-up}$ in SNZ-plus media<$DFI_{neat}$ confirming the observations in case of Volunteers A and B. Further, it is observed that $DFI_{swim-up}$ in commercial medium>$DFI_{neat}$, clearly demonstrating the superiority of the SNZ Plus media over the commercial medium.

Figure 11:
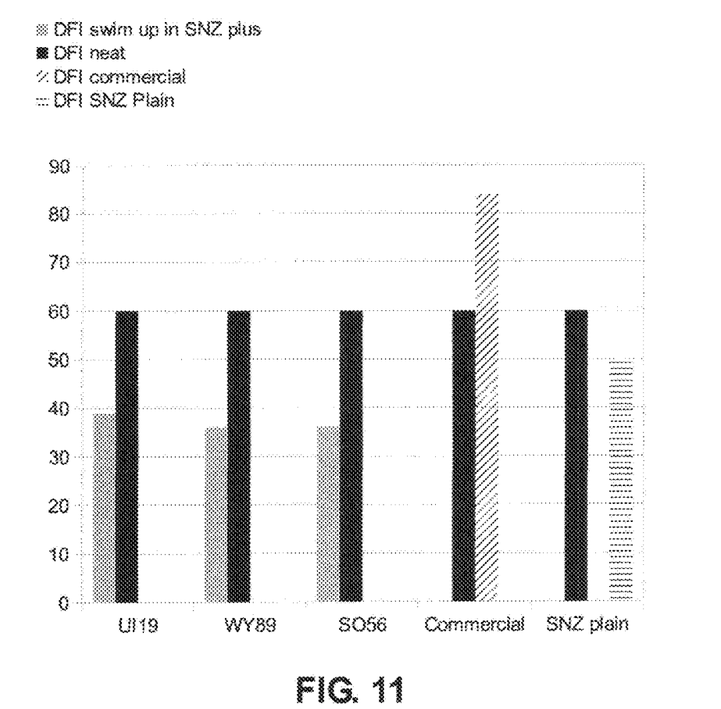
FIG. 11: Bar Chart of DFI before and after swim-UP in SNZ Plus media (UI19, WY89 and SO56) in comparison with the DFI in SNZ plain, in a commercial medium and the neat sample obtained from Volunteer C. $DFI_{SWIM-UP}$ in SNZ Plus media$<DFI_{NEAT}$ and $DFI_{SWIM-UP}$ in commercial medium$>DFI_{NEAT}$.
Figure 12:
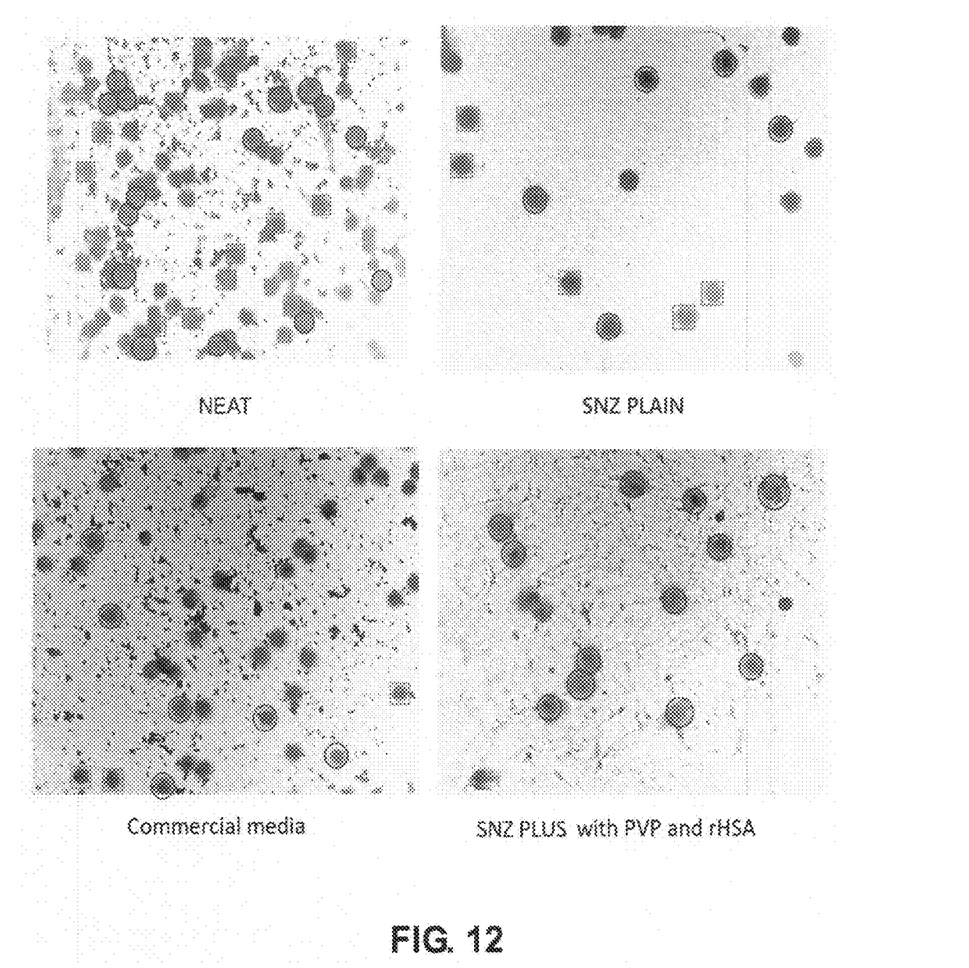
FIG. 12: Pictures of halos under bright field microscopy of neat, post swim-up in SNZ-Plain medium, post swim-up in commercial medium and post swim-up in SNZ-Plus media. Hazy non-distinct halos are seen in the samples after swim-up in commercial medium, in contrast to the clear and only BIG halos in samples after swim-up in SNZ-Plus media.

FIG. 11 illustrates i) DFI of the sperms in the post swim-up fractions in SNZ Plus media are found to be significantly less (approximately 35%) as compared to the neat sample (60%) and ii) DFI of the sperms in the post swim-up fractions in SNZ-Plain is ~50%, and in commercial medium is ~84%.

These results again confirm that progressively motile non-fragmented/intact DNA sperms are enriched, and concentrated in the top layer i.e. the swim-up fraction in the SMA Plus media and if used in assisted reproductive methodologies has the potential to enhance the probability of successful fertilization.

TABLE 6

Results of swim-up with sample obtained from
Volunteer C in SNZ-plus media, SNZ Plain medium,
commercial medium and neat (without swim-up).

| Parameter | Neat | SNZ-Plain Medium | Commercial Medium | SNZ-Plus Medium | | |
|---|---|---|---|---|---|---|
| | | | | UI19 | WY89 | SO56 |
| Count | 150 | 50 | 50 | 46 | 42 | 36 |
| Total Motility (% age) | 70 | 100 | 100 | 100 | 100 | 100 |
| Progressive Motility (% age) | 40 | 100 | 100 | 100 | 100 | 100 |
| Non-Progressive Motility (%) | 30 | 0 | 0 | 0 | 0 | 0 |
| Immotile (%) | 10 | 0 | 0 | 0 | 0 | 0 |
| Dead (%) | 20 | 0 | 0 | 0 | 0 | 0 |
| Yield (%) | 100 | 33 | 33 | 30 | 28 | 24 |
| % (Big) | 22 | 25 | 14 | 0 | 13 | 12 |
| % (Big and Medium) | 39 | 50 | 16 | 60 | 64 | 64 |
| DNA Fragmentation Index (DFI) | 60 | 50 | 84 | 39 | 36 | 36 |

The above experiments demonstrate:
1. Percentage of Sperms containing Big and Medium Halos after swim-up is higher in SNZ Plus medium as compared to those in SNZ Plain medium.

All the experiments show significant reduction (50-70%) of the sperms with small halo/and without halo in SNZ Plus compared to SNZ Plain and Commercial media Thus, post swim-up fractions in SNZ Plus media result in more genetically good or intact DNA spermatozoa as compared to the post swim-up fractions obtained in the commercial medium and in the SNZ Plain medium. SNZ Plus medium offers significantly enhanced enrichment of highly progressive spermatozoa in post swim-up fractions as compared to swim-ups in other media and therefore provides better selection of spermatozoa for therapeutic purposes.

SNZ Plus medium offers separation of highly progressive spermatozoa that cannot be differentiated by regular media and sperms separated using the SNZ Plus media 100% superior in terms of motility that narrows down the selection of other spermatozoa for the therapeutic purposes. IVF or ICSI results can be improved and miscarriage rates can be reduced by using the sperms separated out of SNZ Plus media as they offer higher % of Genetically Normal Forms.

The SNZ Plus media provides a quick and easy method for the collection of enriched fractions of right sperms for therapeutic purposes compared to existing techniques.

SNZ Plus media supports the sperm survival for 48 hrs which is equivalent to presently available commercial media.

SNZ Plus media separated sperms may result in high blastocyst formation rates.

We claim:

1. A swim-up medium for selective enrichment of fractions containing DNA-intact sperm cells post swim-up having a DNA fragmentation index (DFI) with $DFI_{post\ swim-up}$<$DFI_{neat}$, from a semen sample, the swim-up medium comprising a solvent and a solute composition, said solute composition at a concentration of up to 15% w/v, and said solute composition further comprising:
   a. a combination of electrolytes at a concentration range of 10% to 50% w/w consisting of sodium chloride, potassium chloride, magnesium sulphate, potassium di-hydrogen orthophosphate, calcium chloride, sodium bicarbonate, sodium phosphate monobasic anhydrous, magnesium chloride and glucose;
   b. a combination of excipients at a concentration range of 1% to 30% w/w consisting of phenol red, HEPES buffer, gentamicin, sodium pyruvate, sodium lactate, glutamine, glycine, L-Arginine, and methionine;
   c. Polyvinylpyrrolidone (PVP) at a concentration range of 3% to 80% w/w; and
   d. recombinant Human Serum Albumin (rHSA) or bovine serum albumin (BSA) at a concentration range of 0.1% to 50% w/w;
   wherein the said solvent is water.

2. A swim-up medium of claim 1, wherein the combination of electrolytes contains approximately: 75.6% by wt. sodium chloride, 3.4% by wt. potassium chloride, 0.4% by wt. magnesium sulphate, 0.5% by wt. potassium di-hydrogen orthophosphate, 0.29% by wt. calcium chloride, 2.9% by wt. sodium bicarbonate, 0.3% by wt. sodium phosphate monobasic anhydrous, 0.9% by wt. magnesium chloride and 15.5% by wt. glucose.

3. A process for the preparation of the swim-up medium as claimed in claim 1 for selective enrichment of fractions containing DNA-intact sperm cells post swim-up, from semen, in steps comprising:
   i) dissolving the solute composition in water for injection to obtain a 1 to 15% w/v solution;
   ii) adjusting the pH to pH 7.2 to 7.6;

iii) filtering through a 0.2 micron filter and bottling in aseptic conditions; and iv) storing at 2-8° C.

4. A process of effecting swim-up of sperm cells using the medium claimed in claim 1, comprising:
  i) providing a standard sterile test tube of 11 mm diameter used for all swim-ups;
  ii) collecting a neat semen sample from a donor and liquifying for the same for 30-45 minutes;
  iii) dispensing 0.7 ml of pre-heated media into the 11 mm diameter test tube;
  iv) loading 0.3 ml of thoroughly mixed liquified neat sample at the bottom of the test tube;
  v) inclining the test tube to about 45 degrees at 37° C. and in a highly humid environment for 30 mins;
  vi) collecting 200 micro litres of swim-up fraction from the top and keeping it at room temperature in a 0.5 ml eppendorf tube for DNA fragmentation test; and
  vii) storing the selectively enriched of fractions containing DNA-intact sperm cells post swim-up wherein the $DFI_{post\ swimup} < DFI_{neat}$ for further use.

* * * * *